United States Patent [19]

Zipperer et al.

[11] Patent Number: 4,897,425
[45] Date of Patent: Jan. 30, 1990

[54] FUNGICIDAL CYCLOHEXYLAMINES

[75] Inventors: Bernhard Zipperer, Dirmstein; Ernst Buschmann, Ludwigshafen; Norbert Goetz, Worms; Ulrich Schirmer, Heidelberg; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 120,670

[22] Filed: Nov. 16, 1987

[30] Foreign Application Priority Data

Nov. 25, 1986 [DE] Fed. Rep. of Germany ....... 3640247

[51] Int. Cl.[4] ............................................. C07C 101/72
[52] U.S. Cl. .................................... 514/649; 514/653; 514/654; 514/655; 514/659; 514/660; 564/336; 564/340; 564/348; 564/349; 564/355; 564/374; 564/384; 564/389; 564/452
[58] Field of Search .............. 564/452, 391, 336, 340, 564/348, 349, 355, 374, 384, 389; 514/660, 649, 653, 654, 655, 657

[56] References Cited

U.S. PATENT DOCUMENTS

| | | | |
|---|---|---|---|
| 2,192,927 | 3/1940 | Morrill | 564/391 |
| 2,511,028 | 6/1950 | Whitman | 162/161 |
| 3,046,280 | 7/1962 | Kvolt et al. | 564/391 |
| 3,697,594 | 10/1972 | Knowles | 564/452 |
| 3,981,766 | 9/1976 | Pechhold | 564/452 |

FOREIGN PATENT DOCUMENTS

| | | | |
|---|---|---|---|
| 134499 | 7/1984 | European Pat. Off. | 564/452 |
| 259977 | 8/1987 | European Pat. Off. | |
| 1214471 | 10/1966 | Fed. Rep. of Germany | 564/452 |
| 2330454 | 5/1979 | Fed. Rep. of Germany | 564/452 |

OTHER PUBLICATIONS

*J. Org. Chem.*, 1983, 48 pages 3412–3422, Stereoselective Reductions of Substituted Cyclohexyl and Cyclopentyl Carbon–Nitrogen $\pi$ Systems with Hydride Reagents[1].

Primary Examiner—Richard L. Raymond
Assistant Examiner—Raymond Covington
Attorney, Agent, or Firm—Oblon, Spivak, McClelland, Maier & Neustadt

[57] ABSTRACT

Cyclohexylamines of the formula

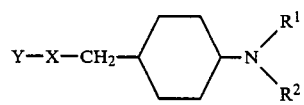

where X is a single bond or an alkylene chain, Y is hydrogen or an aryl, cyclohexyl, 4-cyclohexylcyclohexyl, perhydro-1- or 2-naphthyl or piperidyl radical, $R^1$ and $R^2$ are hydrogen, alkyl, alkenyl, alkynyl, hydroxyalkyl, cycloalkyl, cycloalkenyl or arylalkyl, or $R^1$ and $R^2$ together form an alkylene group and, together with the N atom, form a ring, and acid addition salts thereof, with the exception of compounds in which X is a single bond, Y is cyclohexyl, $R^1$ and $R^2$ are hydrogen or methyl, and the compounds in which X is $C_6$-, $C_7$- and $C_8$-alkyl, Y is hydrogen and $R^1$ and $R^2$ together with the N atom whose substituents they are form a 2,6-dimethylmorpholine radical, and fungicides containing such cyclohexylamines.

12 Claims, No Drawings

FUNGICIDAL CYCLOHEXYLAMINES

BACKGROUND OF THE INVENTION

1. Field of the Invention

The present invention relates to 4-substituted cyclohexylamines, processes for their preparation, their use as fungicides, fungicidal agents, and methods of controlling harmful fungi with these active ingredients.

2. Discussion of the Background

The compound 4-trans-tert.-butyl-N-benzylcyclohexylamine is known (J. Org. Chem. 48 (1983), 3412-3422). However, nothing is known concerning a fungicidal action.

N-Alkyl derivatives of 4-tert.-butylcyclohexylamine, where alkyl may be of 8 to 12 carbon atoms, are described as microbicides (German Laid-Open Application DOS 2,330,454).

The cyclohexylamines of the formula

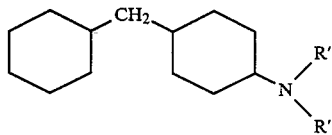

where R' is hydrogen or methyl, are known as fungicides (U.S. Pat. No. 3,981,766).

2,6-Dimethylmorpholines having alkyl-substituted cyclohexyl radicals on N have been described as fungicides (DE 1,214,471).

SUMMARY OF THE INVENTION

We have found that cyclohexylamines of the formula I

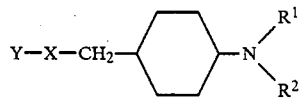

where X is a single bond or an alkylene chain of 1 to 12 carbon atoms which is unsubstituted or substituted by one or more alkyl groups, each of 1 to 5 carbon atoms, and in which 1 to 4 carbon atoms may be replaced by O, S, or N, Y is hydrogen, aryl, cyclohexyl, 4-cyclohexylcyclohexyl, perhydro-1- or -2-naphthyl or piperidyl which may be substituted by one, two or three alkyl, alkoxy, alkylthio or alkylamino groups of 1 to 12 carbon atoms or dialkylamino groups of 2 to 24 carbon atoms or by one, two or three halogen, amino, hydroxyl or trifluoromethyl groups, and $R^1$ and $R^2$ are identical or different and independently of one another are each hydrogen, alkyl, alkenyl, alkynyl, hydroxyalkyl, cycloalkyl, cycloalkenyl or aralkyl of 1 to 12 carbon atoms, which in turn may be substituted by one, two or three alkyl, alkenyl, alkynyl, alkoxy or alkylthio radicals of 1 to 4 carbon atoms or cyclohexyl or 4-tert-butylcyclohexyl, or $R^1$ and $R^2$ together form an alkylene group of 2 to 6 carbon atoms and, together with the N atom, form a ring in which up to three carbon atoms may be replaced by O, S or N and which in turn may have one, two or three alkyl substituents of 1 to 4 carbon atoms, and their addition salts with acids, with the exception of the compounds in which X is a single bond, Y is cyclohexyl and $R^1$ and $R^2$ are each hydrogen or $R^1$ and $R^2$ are each methyl, and the compounds in which X is $C_6$-, $C_7$- or $C_8$-alkyl, Y is hydrogen and $R^1$ and $R^2$, together with the N atom at which they are substituents, form a 2,6-dimethylmorpholine radical, have a powerful fungicidal action.

DETAILED DESCRIPTION OF THE PREFERRED EMBODIMENT

The novel compounds can be used as fungicides. The salts of the novel amines may contain any desired inorganic or organic anions, for example anions of hydrochloric acid, hydrobromic acid, sulfuric acid, nitric acid, acetic acid, higher fatty acids or arylsulfonic acids.

The novel amines of the formula I may contain chiral centers. They are generally obtained as racemates and may be obtained as diasteromer mixtures. In the case of some of the novel compounds, individual diastereomers can be isolated in pure form, for example by distillation or column chromatography or on the basis of solubility differences. Pure racemates and enantiomers can be obtained from such purified diasteromers by known methods. The present invention relates to all these compounds and mixtures. Regarding the use of the novel amines as fungicides, both the pure diastereomers and enantiomers and their mixtures obtained in the synthesis are suitable. The latter are preferably used. X is, for example, $C_1$-$C_4$-alkylene, eg. methylene, ethylene, 1,2-propylene, 1,3-propylene, 1,3-butylene, 1,4-butylene, 2-alkyl-1,3-propylene, 2,2-dialkyl-1,3-propylene, 1,5-pentylene and, for example, 2-alkyl-1,4-butylene, 2-alkyl-1,5-pentylene, 3-alkyl-1,5-pentylene, 1,6-hexylene, 2-alkyl-1,6-hexylene, 1,7-heptylene, 1,8-octylene, 1,9-nonylene, 1,10-decylene, 1,11-undecylene, 1,12-dodecylene, methyleneoxy, ethyleneoxy, propyleneoxy, butyleneoxy, pentyleneoxy, hexyleneoxy, heptyleneoxy, octyleneoxy, nonyleneoxy, decyleneoxy, undecyleneoxy, dodecyleneoxy, ethyleneamino, propyleneamino or N-$C_1$-$C_4$-alkylpropyleneamino.

Y is, for example, hydrogen, phenyl, $C_1$-$C_4$-alkylphenyl, cyclohexyl, $C_1$-$C_4$-alkylcyclohexyl, 2-, 3- or 4-methylcyclohexyl, 2-, 3- or 4-ethylcyclohexyl, 2-, 3- or 4-propylcyclohexyl, 2-, 3- or 4-isopropylcyclohexyl, 2-, 3- or 4-n-butylcyclohexyl, 2-, 3- or 4-tert-butylcyclohexyl, 4-cyclohexylcyclohexyl, dimethylcyclohexyl, methylethyl-cyclohexyl, methylisopropylcyclohexyl, methyl-tert-butyl-cyclohexyl, diethylcyclohexyl, ethylisopropylcyclohexyl, ethyl-tert-butylcyclohexyl, halocyclohexyl, 2-, 3- or 4-chlorocyclohexyl, 2-, 3- or 4-fluorocyclohexyl, 2-, 3- or 4-trifluoromethylcyclohexyl, 2-, 3- or 4-aminocyclohexyl, $C_1$-$C_{12}$-alkylaminocyclohexyl, $C_2$-$C_{24}$-dialkylaminocyclohexyl, hydroxycyclohexyl, $C_1$-$C_{12}$-alkoxycyclohexyl, $C_1$-$C_{12}$-alkylthiocyclohexyl, perhydro-1-naphthyl, perhydro-2-naphthyl, 1-, 2-, 3- or 4-piperidyl, 1-($C_1$-$C_{12}$-alkyl)-2-, 3- or 4-piperidyl.

$R^1$ and $R^2$ are each, for example, $C_1$-$C_{10}$-alkyl, methyl, ethyl, straight-chain or branched propyl, butyl, pentyl, hexyl, heptyl, octyl, nonyl, decyl, 2-hydroxypropyl, $C_2$-$C_5$-alkenyl, allyl, methallyl, pentenyl, cyclopentyl, cyclohexyl, cyclohexylmethyl, tert-butylcyclohexylmethyl, methylcyclohexyl, tert-butylcyclohexyl, cycloheptyl, cyclooctyl, benzyl, $C_1$-$C_4$-alkylbenzyl, methylbenzyl, ethylbenzyl, dimethylbenzyl, methylethylbenzyl, isopropylbenzyl or tert-butylbenzyl, or $R^1$ and $R^2$, together with the nitrogen atom at which they are substituents, form the radical of aziridine, pyrrolidine, mono-, di- or trimethyl- pyrrolidine, piperidine, mono-, di- or trimethylpiperidine, ethyl-piperidine, propylpiperidine, tert-butylpiperidine, phenylpiperidine, morpholine, thiomorpholine, 2- or 3-methylmorpholine, 2,5-dimethylmorpholine, 2,6-dimethylmorpholine (cis/trans or cis or trans), 2,6-dimethylthiomorpholine, piperazine, methyl-, ethyl-, propyl- or tert-butylpiperazine or hexamethyleneimine.

The compounds in which X is methylene or 1,2-ethylene, Y is cyclohexyl or perhydronaphthyl and $R^1$ and $R^2$ are each hydrogen are preferred.

Secondary and tertiary amines of the formula I can be prepared from the corresponding primary amines of the formula II, for example by stepwise alkylation.

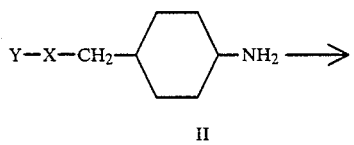

II

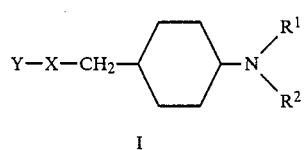

I

These alkylation reactions can be carried out, for example, as follows:
(a) with compounds of the formulae III and IV

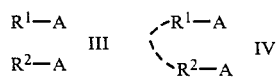

where $R^1$ and $R^2$ have the abovementioned meanings, with the exception of hydrogen, and A is a nucleophilically displaceable leaving group, for example chlorine, bromine, alkylsulfonyl or arylsulfonyl. The compounds III and IV are known and are readily available commercially. Suitable solvents or diluents for the reaction are, for example, halohydrocarbons, in particular chlorohydrocarbons, eg. dichloromethane, trichloromethane, tetrachloromethane, 1,2-dichloroethane, 1,1,1- or 1,1,2-trichloroethane, trichloroethylene, chlorobenzene, chlorotoluenes, dichlorobenzenes or ethers, eg. diethyl ether, methyl tert-butyl ether, diisopropyl ether, diisobutyl ether, di-n-butyl ether, ethylene glycol dimethyl ether, tetrahydrofuran or dioxane. It is also possible to use polar solvents, such as acetone, methyl ethyl ketone, acetonitrile, dimethylformamide, N-methylpyrrolidone, ethyl acetate, nitromethane or dimethyl sulfoxide. Instead of a solvent, the alkylating agents of the formulae III and IV may also be used in excess. Suitable auxiliary bases (acid acceptors) for the reaction to give compounds of the formula I are all conventional acid acceptors. These preferably include tertiary amines, alkali metal and alkaline earth metal oxides, hydroxides and salts, and basic ion exchangers.

Examples of suitable basic compounds are potassium hydroxide, sodium hydroxide, calcium hydroxide, barium hydroxide, calcium oxide, barium oxide, magnesium oxide, potassium carbonate, sodium carbonate, sodium bicarbonate, sodium acetate, triethylamine, tri-n-propylamine, tri-n-butylamine , ethyldiisopropylamine, N,N-dimethylcyclohexylamine, pyridine, methylpyridines, quinoline, isoquinoline, 2,6-lutidine and 2,4,6-collidine.

The alkylation reactions can also be carried out, for example,
(b) with aldehydes or ketones of the general formulae

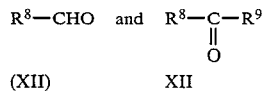

where $R^8$ and $R^9$ correspond to the radicals $R^1$ and $R^2$, with the proviso that they have one carbon atom less than $R^1$ and $R^2$, ie. $C_1$-$C_{11}$-alkyl, -alkenyl, -alkynyl, -hydroxyalkyl, -cycloalkyl, -cycloalkenyl or -aralkyl, which in turn may be substituted by one, two or three straight-chain or branched alkyl, alkenyl, alkynyl, alkoxy or alkylthio radicals of 1 to 4 carbon atoms or cyclohexyl or 4-tert-butylcyclohexyl.

The aldehydes and ketones are reacted with the relevant primary or secondary amines in the presence of a reducing agent, advantageously in a solvent and in the presence or absence of a catalyst; however, they may also first be reacted with the relevant primary or secondary amines to give imines or enamines, which are then reduced to the amines of the formula I, in the presence or absence of a catalyst.

The aldehydes and ketones are known compounds and are readily obtainable commercially.

Examples of suitable reducing agents for carrying out the novel process are complex hydrides, preferably lithium borohydride, sodium borohydride, sodium cyanoborohydride, lithium aluminum hydride, lithium tri-tert-butoxyaluminum hydride and lithium-tri-(2-methylbut-2-yl) borohydride. Another suitable reducing agent is hydrogen in the presence of a catalyst, for example a noble metal, preferably palladium, which may have been applied on a carrier, eg. active carbon, and formic acid (Leuckart-Wallach reaction; cf. Methoden der Org. Chemie (Houben-Weyl), vol. XI/1 (1957), page 648 et seq.).

Depending on the type of reducing agent used, it is possible to use aprotic or protic solvents, for example ethers, preferably diethyl ether, tetrahydrofuran, dioxane or ethylene glycol dimethyl ether, esters, preferably ethyl acetate, or alcohols, preferably methanol, ethanol, propanols or butanols.

The primary amines II used for the alkylation are also novel. They can be prepared, for example, by first reducing phenylnitro compounds of the formula V

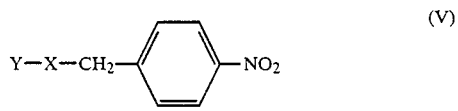

by a known method (cf. for example Methoden der Organischen Chemie (Houben-Weyl), volume XI/1 (1957), pages 360–515) to give the corresponding anilines, and then hydrogenating these with hydrogen in the presence of a catalyst under superatmospheric pressure by a conventional process (cf. European Patent 53,818).

The intermediates of the formula V are novel and can be prepared by various processes, for example by
(a) reacting phosphonium salts of the formula VI $$Y\text{-}X\text{-}P\oplus(C_6H_5)_3\text{-}Hal\ominus \qquad (VI)$$

where X and Y have the abovementioned meanings and Hal⊖ is chloride or bromide, with 4-nitrobenzaldehyde in the presence of a base in a solvent.

The phosphonium salts (VI) are obtainable by reacting the corresponding halides Y-X-Hal with triphenylphosphine in a solvent, for example benzene, toluene or xylene, at elevated temperatures, preferably from 80° to 130° C.

Examples of suitable bases for the reaction of the phosphonium salts (VI) with 4-nitrobenzaldehyde are alkali metal hydroxides, alcoholates and hydrides and organometallic compounds, for example sodium hydroxide, potassium hydroxide, sodium methylate, sodium ethylate, potassium tert-butylate, sodium hydride, potassium hydride, n-butyllithium, sec-butyllithium, tert-butyllithium, phenyllithium, methyllithium or lithiumdiisopropylamide. Depending on the type of base used, suitable solvents are protic or aprotic solvents, for example alcohols, such as methanol, ethanol or tert-butanol, ethers, eg. diethyl ether, tetrahydrofuran, dioxane or ethylene glycol dimethyl ether, and if necessary also benzene or dimethyl sulfoxide (cf. Methoden der Organischen Chemie (Houben-Weyl) vol. V/1 (1972), page 383 et seq.).

Intermediates of the formula V can also be prepared by (b) reacting aldehydes of the formula VII

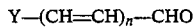     Y—(CH=CH)$_n$—CHO     VII where Y has the abovementioned meanings and n may be 0 or 1, with 4-nitroacetophenone in the presence of a catalyst.

Suitable catalysts for this condensation are both acidic and basic substances. Examples of suitable acids are hydrochloric acid, sulfuric acid, boric acid, acetic acid and arylsulfonic acids, while examples of suitable bases are alkali metal and alkaline earth metal oxides, hydroxides and alcoholates, eg. sodium hydroxide, barium hydroxide, sodium methylate, sodium ethylate and potassium tert-butylate.

The aldehydes VII are known compounds and are readily obtainable commercially.

The condensations can be carried out in the presence or absence of a diluent.

Suitable diluents are protic and aprotic solvents, for example alcohols, eg. methanol, ethanol, propanols or butanols, if necessary also as a mixture with water, hydrocarbons, eg. benzene, toluene or xylenes, ethers, eg. dimethyl ether, tetrahydrofuran or dioxane, and sulfoxides, eg. dimethyl sulfoxide.

Depending on the type of catalyst used, the reactions can be carried out at low temperatures, preferably from −10° to +30° C. or at elevated temperatures, preferably at +40° to +150° C., and may be accelerated by removing the water of reaction formed.

Intermediates of the formula V can also be prepared by (c) reacting an aromatic compound of the formula VIII

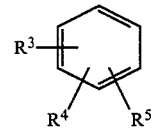

where $R^3$, $R^4$ and $R^5$ are each one of the substituents of the aryl radical which have been defined for Y, with 4-nitrobenzoyl chloride in the presence of a Lewis acid and in the presence or absence of a solvent or diluent, and then reducing the resulting diaryl ketone, for example with hydrazine/potassium hydroxide (Wolff-Kishner reduction, cf. D. Todd, Org. Reactions 4 (1948), 378–422) or with a metal or metal alloy, for example zinc amalgam (Clemmensen reduction, cf. E. L. Martin, Org. Reactions 1 (1942), 155–209).

The aromatic compounds of the formula VIII are known and are readily obtainable commercially. VIII comprises, for example, hydrocarbons, such as benzene, toluene, xylenes, ethylbenzene, cumene, tert-butylbenzene, biphenyl, naphthalene, phenanthrene or anthracene, halohydrocarbons, eg. fluorobenzene, chlorobenzene, bromobenzene or chloronaphthalenes, and aryl ethers, eg. anisole, phenetole, tert-butoxybenzene, methoxynaphthalenes or diphenyl ether.

Suitable Lewis acids for the reaction of compounds of the formula VIII with 4-nitrobenzoyl chloride are anhydrous halides, for example boron trichloride, aluminum trichloride, phosphorus trichloride, or zinc chloride.

The reaction of compounds of the formula VIII with 4-nitrobenzoyl chloride can be carried out in the presence or absence of a diluent. Example of suitable diluents are halohydrocarbons, eg. dichloromethane or 1,2-dichloroethane, and other solvents which are inert under the reaction conditions, eg. carbon disulfide and nitrobenzene.

Intermediates of the formula V can also be prepared by (d) condensing a compound of the formula IX

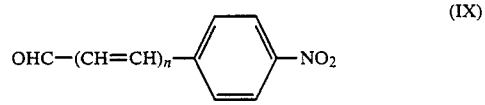

where n may be 0 or 1, with 2- or 4-methylpyridine in the presence of a catalyst.

The aldehydes of the formula IX are known and are commercially available. The reaction with 2- or 4-methylpyridine is advantageously carried out in the presence of an acidic catalyst, eg. anhydrous zinc chloride or acetic anhydride, at elevated temperatures, preferably 140°–230° C.

Intermediates of the formula V can also be prepared by (e) reacting a compound of the formula X

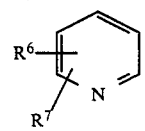

where R⁶ and R⁷ are each one of the substituents of the pyridine radical which have been defined for Y, with a compound of the formula XI

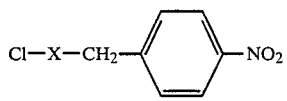
(XI)

where X has the abovementioned meanings, in a solvent, and hydrogenating the reaction product.

The pyridine derivatives of the formula X are known and are readily obtainable commercially. They are, for example, pyridine, 2-, 3- and 4-picoline, 2-, 3- and 4-ethylpyridine, 2-, 3- and 4-propylpyridine, 2-, 3- and 4-isopropylpyridine, 2-, 3- and 4-phenylpyridine, 4-tert-butylpyridine, 2,6-lutidine, 2,4,6-collidine, quinoline, 2-, 3- and 4-mthylquinoline and isoquinoline.

The ω-(4-nitrophenyl)alkyl chlorides of the formula XI are known. Examples of these compounds are 4-nitrobenzyl chloride, 2-(4-nitrophenyl)ethyl chloride, 3-(4-nitrophenyl)propyl chloride, 2-(4-nitrophenyl)propyl chloride and 4-(4-nitrophenyl)butyl chloride.

Suitable solvents for the reaction of the compounds X and XI are both highly polar protic and aprotic solvents, for example alcohols, in particular methanol, ethanol, propanols or butanols, esters, in particular methyl acetate or ethyl acetate, nitriles, eg. acetonitrile or propionitrile, amides, eg. dimethylformamide, N-methylformanilide or N-methylpyrrolidone, and nitro compounds, preferably nitromethane, 1- or 2-nitropropane or nitrobenzene. The reactions are carried out in general at from +20° to +200° C., under atmospheric or superatmospheric pressure.

Method 1

4-Methyl-1-(4-nitrobenzyl)pyridinium chloride

A solution of 34.4 g (0.2 mole) of 4-nitrobenzyl chloride and 27.9 g (0.3 mole) of 4-methylpyridine in 200 ml of acetonitrile is refluxed for 8 hours. The solution is evaporated down to about half its volume and cooled to 0° C., and the precipitate which separates out is filtered off under suction, washed thoroughly with ether and dried under reduced pressure to give 37.6 g (71% of theory) of the title compound of melting point 220°–222° C.

Method 2

2-(4-Nitro-trans-styryl)pyridine

A solution of 46.5 g (0.5 mole) of 2-methylpyridine and 75.5 g (0.5 mole) of 4-nitrobenzaldehyde in about 100 g of acetic anhydride (about 1 mole) is refluxed for 6 hours, after which it is carefully poured onto ice water. The stirred mixture is neutralized with saturated, aqueous sodium bicarbonate solution. The precipitate is filtered off under suction, washed with water and recrystallized from ethanol to give 66 g (63% of theory) of reddish brown crystals of melting point 136°–139° C.

Method 3

4-Nitro-4'-phenylbenzophenone

A solution of 147 g (1.05 moles) of 4-nitrobenzoyl chloride in 250 ml of 1,2-dichloroethane and a solution of 154 g (1.0 mole) of biphenyl in 200 ml of 1,2-dichloroethane are added dropwise, in succession, to the suspension of 160 g (1.2 moles) of anhydrous aluminum chloride in 400 ml of 1,2-dichloroethane at 0° C. The mixture is allowed to reach room temperature, after which it is stirred for 2 hours at 50° C. and poured carefully onto ice water. The precipitate is filtered off under suction, washed thoroughly with water and recrystallized from ethanol to give 230 g (89% of theory) of brown crystals of melting point 174°–176° C.

Method 4

E-(3-Methylstyryl) 4-nitrophenyl ketone 10 g of boric acid are added to a solution of 76 g (0.63 mole) of 3-methylbenzaldehyde and 104.5 (0.63 mole) of 4-nitroacetophenone in 1 l of xylene, and the mixture is refluxed for 8 hours under a water separator. A further 5 g of boric acid are added, after which the mixture is boiled for a further 8 hours. This process is repeated until the theoretical amount of water has been separated off (2–3 times). The cooled reaction mixture is filtered under suction and the residue is washed with toluene and dried under reduced pressure to give 131 g (77% of theory) of a yellowish brown powder of melting point 130°–132° C.

Method 5

4-[3-(3-Methylphenyl)-propyl]aniline 46 g (0.47 mole) of concentrated sulfuric acid and 8 g of palladium on 80% active carbon are added to a solution of 130 g (0.49 mole) of E-(3-methylstyryl) 4-nitrophenyl ketone in 1.3 l of glacial acetic acid, and the mixture is saturated with nitrogen. Thereafter, hydrogen gas is passed into the stirred mixture under atmospheric pressure. After about 30 l of hydrogen has been absorbed, the mixture is heated to 50°–70° C. and hydrogenated until the theoretical amount of hydrogen (about 66 l) has been consumed. The mixture is filtered under suction over kieselguhr, the filtrate is evaporated to dryness and the residue is stirred with 1 l of ice water, 200 ml of 50% strength sodium hydroxide solution and 800 ml of methyl tert-butyl ether. The aqueous phase is washed with 3 times 250 ml of methyl tert-butyl ether, and the combined organic phases are washed once with 250 ml of water and once with 250 ml of saturated NaCl solution, dried over Na₂SO₄ and evaporated down under reduced pressure to give 114 g of a brown oil of boiling point 158°–163° C./0.3 mm, which is about 95% pure (corresponding to 98% of theory) according to the gas chromatogram.

EXAMPLE 1

Cis,trans-4-[3(3-methylcyclohexyl)-propyl]cyclohexylamine 0.5 g of ruthenium dioxide is added to a solution of 63 g (0.28 mole) of 4-[3-(3-methylphenyl)-propyl]aniline in 100 ml of dioxane, and hydrogenation is carried out in a 300 ml stirred autoclave at 140° C. and under an H₂ pressure of 300 bar until the pressure remains constant (about 3 hours). The discharged mixture is filtered under suction over kieselguhr, the filtrate is evaporated down under reduced pressure and the residue is subjected to fractional distillation to give 47 g (71% of theory) of a colorless oil of boiling point 100°–116° C./0.2 mm, consisting of about 30% of the cis isomer and 70% of the trans isomer (compound no. 64).

EXAMPLE 2

(4-tert-Butylbenzyl)-4-[3-(3-methylcyclohexyl)-propyl]cyclohexylamine

A solution of 11.9 g (0.05 mole) of 4-[3-(3-methylcyclohexyl)-propyl]cyclohexylamine in 50 ml of anhydrous methanol is acidified to pH 5-6 with a methanolic HCl solution, after which 8.1 g (0.05 mole) of 4-tert-butylbenzaldehyde and 15 g of dry molecular sieve (3 Å, Grace type 0564) are added and the mixture is cooled to 0° C. 1.6 g (0.025 mole) of sodium cyanoborohydride are added a little at a time to the stirred mixture, the latter is heated to room temperature and stirring is continued for 24 hours. Thereafter, the mixture is acidified with concentrated HCl, hydrogen cyanide formed is expelled by means of nitrogen, and the mixture is filtered and rendered alkaline with dilute NaOH. It is extracted several times with dichloromethane, the organic phase is dried over $MgSO_4$ and evaporated down, and the residue is distilled to give 9.5 g (56% of theory) of a yellow oil of boiling point 236°–242° C./0.4 mm (compound no. 65).

The following compounds can be prepared in a similar manner:

TABLE 1

| Example No. | X | Y | $R^1$ | $R^2$ | Physical data bp. or mp. |
|---|---|---|---|---|---|
| 1 | — | Cyclohexyl | —$CH_2CH(OH)CH_3$ | —$CH_2CH(OH)CH_3$ | 150–153° C./0.2 mm |
| 2 | — | Cyclohexyl | —$CH_2CH(CH_3)OCH(CH_3)CH_2$— | | |
| 3 | — | Cyclohexyl | —$CH_2CH_2$— | | |
| 4 | — | Cyclohexyl | —$CH_2(CH_2)_2CH_2$— | | |
| 5 | — | Cyclohexyl | —$CH_2(CH_2)_3CH_2$— | | |
| 6 | — | 4-Methylcyclohexyl | H | H | |
| 7 | — | 4-Methylcylohexyl | H | —$CH_2(p-C_6H_4)C(CH_3)_3$ | |
| 8 | — | 4-Chlorocylcohexyl | H | H | |
| 9 | — | 4-Chlorocylcohexyl | H | —$CH_2(p-C_6H_4)C(CH_3)_3$ | |
| 10 | — | 4-Fluorocyclohexyl | H | H | |
| 11 | — | 4-Fluorocyclohexyl | H | —$CH_2(p-C_6H_4)C(CH_3)_3$ | |
| 12 | — | 1-Piperidyl | H | H | |
| 13 | — | 1-Piperidyl | H | —$CH_2(p-C_6H_4)C(CH_3)_3$ | |
| 14 | — | Perhydro-2-naphthyl | H | H | 127–131° C./0.3 mm |
| 15 | $CH_2$ | Cyclohexyl | H | H | |
| 16 | $CH_2$ | Cyclohexyl | $CH_3$ | $CH_3$ | |
| 17 | $CH_2$ | Cyclohexyl | H | —$CH_2(p-C_6H_4)C(CH_3)_3$ | |
| 18 | $CH_2$ | 4-Methylcyclohexyl | H | H | 116–122° C./0.5 mm |
| 19 | $CH_2$ | 4-Methylcyclohexyl | | —$CH_2(p-C_6H_4)C(CH_3)_3$ | |
| 20 | $CH_2$ | 4-Trifluoromethyl-cyclohexyl | H | H | |
| 21 | $CH_2$ | 4-Trifluoromethyl-cyclohexyl | H | —$CH_2(p-C_6H_4)C(CH_3)_3$ | |
| 22 | $CH_2$ | 4-tert.-Butylcyclohexyl | H H | H | 132–140° C./0.2 mm |
| 23 | $CH_2$ | 4-tert.Butylcyclohexyl | —$CH_2CH(CH_3)OCH(CH_3)CH_2$— | | 233–240° C./0.4 mm |
| 24 | $CH_2$ | 4-tert.Butylcyclohexyl | H | —$CH_2(p-C_6H_4)C(CH_3)_3$ | |
| 25 | $CH_2$ | Perhydro-1-naphthyl | H | H | 152–154° C./0.3 mm |
| 26 | $CH_2$ | Perhydro-1-naphthyl | —$CH_2CH(CH_3)OCH(CH_3)CH_2$— | | 200–208° C./0.4 mm |
| 27 | $CH_2$ | 4-Fluorocyclohexyl | H | H | |
| 28 | $CH_2$ | 4-Fluorocyclohexyl | H | —$CH_2(p-C_6H_4)C(CH_3)$ | |
| 29 | $CH_2$ | 4-Chlorocyclohexyl | H | H | |
| 30 | $CH_2$ | 4-Chlorocyclohexyl | H | —$CH_2(p-C_6H_4)C(CH_3)$ | |
| 31 | $CH_2$ | 4-Chlorocyclohexyl | —$CH_2(CH_2)_3CH_2$— | | |
| 32 | $CH_2$ | 3-Chlorocyclohexyl | H | H | |
| 33 | $CH_2$ | 3-Chlorocylcohexyl | H | —$CH_2(p-C_6H_4)C(CH_3)$ | |
| 34 | $CH_2$ | 2-Chlorocyclohexyl | H | H | |
| 35 | $CH_2$ | 2-Chlorocyclohexyl | H | —$CH_2(p-C_6H_4)C(CH_3)_3$ | |
| 36 | $CH_2$ | 4-Aminocyclohexyl | H | H | |
| 37 | $CH_2$ | 3-Aminocyclohexyl | H | H | |
| 38 | $CH_2$ | 2-Aminocyclohexyl | H | H | |
| 39 | $CH_2$ | 4[(4-tert.-Butylbenzyl)amino]cyclohexyl | H | —$CH_2(p-C_6H_4)C(CH_3)_3$ | |
| 40 | $CH_2$ | 1-Piperidyl | H | H | |
| 41 | $CH_2$ | 1-Piperidyl | H | —$CH_2(p-C_6H_4)C(CH_3)_3$ | |
| 42 | $CH_2$ | 2-Piperidyl | H | H | |
| 43 | $CH_2$ | 2-(1-Methylpiperidyl) | H | H | |
| 44 | $CH_2$ | 2-(1-Methylpiperidyl) | H | —$CH_2(p-C_6H_4)C(CH_3)_3$ | |
| 45 | $CH_2$ | 2-(1-Methylpiperidyl) | H | H | |
| 46 | $CH_2$ | 3-Piperidyl | H | H | |
| 47 | $CH_2$ | 3-(1-Methylpiperidyl) | H | H | |
| 48 | $CH_2$ | 3-(1-Methylpiperidyl) | H | —$CH_2(p-C_6H_4)C(CH_3)_3$ | |
| 49 | $CH_2$ | 4-Piperidyl | H | H | |
| 50 | $CH_2$ | 4-(1-Methylpiperidyl) | H | H | |
| 51 | $CH_2$ | 4-(1-Methylpiperidyl) | H | —$CH_2(p-C_6H_4)C(CH_3)_3$ | |
| 52 | $CH_2$ | 4-(1-Propylpiperidyl) | H | H | |
| 53 | $(CH_2)_2$ | Cyclohexyl | H | H | |

TABLE 1-continued

| Example No. | X | Y | R¹ | R² | Physical data bp. or mp. |
|---|---|---|---|---|---|
| 54 | (CH₂)₂ | Cyclohexyl | H | —CH₂(p-C₆H₄)C(CH₃)₃ | |
| 55 | (CH₂)₂ | Cyclohexyl | —CH₂CH(OH)CH₃ | —CH₂CH(OH)CH₃ | |
| 56 | (CH₂)₂ | Cyclohexyl | —CH₂CH(CH₃)OCH(CH₃)CH₂— | | 218–220° C./ 0.8 mm |
| 57 | (CH₂)₂ | Cyclohexyl | —CH₂CH₂— | | |
| 58 | (CH₂)₂ | Cyclohexyl | —CH₂(CH₂)₂CH₂— | | |
| 59 | (CH₂)₂ | 4-Methylcyclohexyl | H | H | |
| 60 | (CH₂)₂ | 4-Methylcyclohexyl | CH₃ | CH₃ | |
| 61 | (CH₂)₂ | 4-Methylcyclohexyl | H | —CH₂(p-C₆H₄)C(CH₃)₃ | |
| 62 | (CH₂)₂ | 4-Methylcyclohexyl | —CH₂(CH₂)₂CH₂— | | |
| 63 | (CH₂)₂ | 4-Methylcyclohexyl | —CH₂CH(CH₃)OCH(CH₃)CH₂— | | 190–194° C./ 1.0 mm |
| 64 | (CH₂)₂ | 3-Methylcyclohexyl | H | H | |
| 65 | (CH₂)₂ | 3-Methylcyclohexyl | H | —CH₂(p-C₆H₄)C(CH₃)₃ | |
| 66 | (CH₂)₂ | 2-Methylcyclohexyl | H | H | |
| 67 | (CH₂)₂ | 2-Methylcyclohexyl | —CH₂CH(OH)CH₃— | —CH₂CH(OH)CH₃ | 222–226° C./ 1.5 mm |
| 68 | (CH₂)₂ | 2-Methylcyclohexyl | —CH₂CH(CH₃)OCH(CH₃)CH₂— | | |
| 69 | (CH₂)₂ | 3,4-Dimethylcyclohexyl | H | H | 144–145° C./ 0.8 mm |
| 70 | (CH₂)₂ | 3,4-Dimethylcyclohexyl | —CH₂CH(CH₃)OCH(CH₃)CH₂— | | 195–197° C./ 0.5 mm |
| 71 | (CH₂)₂ | 3,4-Dimethylcyclohexyl | —CH₂CH(CH₃)OCH(CH₃)CH₂— | | |
| 72 | (CH₂)₂ | 4-Ethylcyclohexyl | H | H | 136–144° C./ 0.3 mm |
| 73 | (CH₂)₂ | 4-Ethylcyclohexyl | CH₃ | CH₃ | 140–141° C./ 0.4 mm |
| 74 | (CH₂)₂ | 4-Ethylcyclohexyl | H | —CH₂(p-C₆H₄)C(CH₃)₃ | |
| 75 | (CH₂)₂ | 4-Ethylcyclohexyl | —CH₂CH(CH₃)(OCH(CH₃)CH₂ | | 200° C./ 0.8 mm |
| 76 | (CH₂)₂ | 4-(2-Propyl)cyclohexyl | H | H | 132–134° C./ 0.3 mm |
| 77 | (CH₂)₂ | 4-(2-Propyl)cyclohexyl | H | —CH₂(p-C₆H₄)C(CH₃)₃ | |
| 78 | (CH₂)₂ | 4-(2-Propyl)cyclohexyl | —CH₂CH(CH₃)OCH(CH₃)CH₂— | | 197–200° C./ 0.4 mm |
| 79 | (CH₂)₂ | 4-tert.-Butylcyclohexyl | H | H | |
| 80 | (CH₂)₂ | 4-tert.-Butylcyclohexyl | H | —CH₂(p-C₆H₄)C(CH₃)₃ | |
| 81 | (CH₂)₂ | 4-tert.-Butylcyclohexyl | —CH₂(CH₂)₂CH₂— | | |
| 82 | (CH₂)₂ | 4-Cyclohexylcyclohexyl | H | H | 188–190° C./ 0.4 mm |
| 83 | (CH₂)₂ | 4-Cyclohexylcyclohexyl | H | —CH₂(p-C₆H₄)C(CH₃)₃ | |
| 84 | (CH₂)₂ | 4-Trifluoromethyl-cyclohexyl | H | H | |
| 85 | (CH₂)₂ | 4-Trifluoromethyl-cyclohexyl | H | —CH₂(p-C₆H₄)C(CH₃)₃ | |
| 86 | (CH₂)₂ | 4-Fluorocyclohexyl | H | H | |
| 87 | (CH₂)₂ | 4-Chlorocyclohexyl | H | H | |
| 88 | (CH₂)₂ | 4-Chlorocyclohexyl | H | —CH₂(p-C₆H₄)C(CH₃)₃ | |
| 90 | (CH₂)₂ | 4-Chlorocyclohexyl | H | H | |
| 90 | (CH₂)₂ | 4-Aminocyclohexyl | H | H | |
| 91 | (CH₂)₂ | 4-(N,N—Dimethylamino)-cyclohexyl | H | H | |
| 92 | (CH₂)₂ | 3-Chlorocylcohexyl | H | H | |
| 93 | (CH₂)₂ | 3-Chlorocyclohexyl | H | —CH₂(p-C₆H₄)C(CH₃)₃ | |
| 94 | (CH₂)₂ | 2-Chlorocyclohexyl | H | H | |
| 95 | (CH₂)₂ | 2-Chlorocyclohexyl | H | —CH₂(p-C₆H₄)C(CH₃)₃ | |
| 96 | (CH₂)₂ | 2-Aminocyclohexyl | H | H | |
| 97 | (CH₂)₂ | 3-Aminocyclohexyl | H | H | |
| 98 | (CH₂)₂ | Perhydro-1-naphthyl | H | H | 150–155° C./ 0.3 mm |
| 99 | (CH₂)₂ | Perhydro-1-naphthyl | —CH₂CH(CH₃)OCH(CH₃)CH₂ | | 222–228° C./ 0.5 mm |
| 100 | (CH₂)₂ | Perhydro-1-naphthyl | H | H | 176–184° C./ 0.5 mm |
| 101 | (CH₂)₂ | Perhydro-1-naphthyl | CH₃ | CH₃ | |
| 102 | (CH₂)₂ | Perhydro-1-naphthyl | —CH₂CH(CH₃)OCH(CH₃)CH₂— | | 211–212° C./ 0.4 mm |
| 103 | (CH₂)₂ | 1-Piperidyl | H | H | |
| 104 | —CH(CH₃)CH₂— | Cyclohexyl | H | H | 139–141° C./ 2.0 mm |
| 105 | —CH(CH₃)CH₂— | 4-Methylcyclohexyl | H | H | 144–148° C./ 1.5 mm |
| 106 | —CH(CH₃)CH₂— | 4-Methylcyclohexyl | H | —CH₂(p-C₆H₄)C(CH₃ | |
| 107 | —CH(CH₃)CH₂— | 4-tert.-Butylcyclohexyl | H | H | |
| 108 | —CH(CH₃)CH₂— | 4-tert.-Butylcyclohexyl | H | —CH₂(p-C₆H₄)C(CH₃ | |
| 109 | —CH(CH₃)CH₂ | 4-tert.-Butylcyclohexyl | —CH₂CH(CH₃)OCH(CH₃)CH₂ | | 176° C./ 0.1 mm |
| 110 | —CH(CH₃)CH₂ | 4-tert.-Butylphenyl | H | H | 163° C./ |

TABLE 1-continued

| Example No. | X | Y | R$^1$ | R$^2$ | Physical data bp. or mp. |
|---|---|---|---|---|---|
| | | | | | 0.4 mm |
| 111 | —CH(CH$_3$)CH$_2$— | 4-(2,6-Dimethyl-morpholinyl) | H | H | |
| 112 | —CH$_2$O— | H | H | H | |
| 113 | —CH$_2$O— | H | H | —CH$_2$(p-C$_6$H$_4$)C(CH$_3$)$_3$ | |
| 114 | —CH$_2$O— | Cyclohexyl | H | Cyclohexyl | |
| 115 | —CH$_2$O— | Cyclohexyl | H | —CH$_2$(p-C$_6$H$_4$)C(CH$_3$)$_3$ | |
| 116 | (CH$_2$)$_3$ | Cyclohexyl | H | H | |
| 117 | (CH$_2$)$_3$ | Cyclohexyl | H | —CH$_2$(p-C$_6$H$_4$)C(CH$_3$)$_3$ | |
| 118 | (CH$_2$)$_3$ | 4-Methylcyclohexyl | H | H | |
| 119 | (CH$_2$)$_3$ | 4-Methylcyclohexyl | H | —CH$_2$(p-C$_6$H$_4$)C(CH$_3$)$_3$ | |
| 120 | (CH$_2$)$_3$ | 4-tert.-Butylcyclohexyl | H | H | |
| 121 | (CH$_2$)$_3$ | 4-tert.-Butylcyclohexyl | H | —CH$_2$(p-C$_6$H$_4$)C(CH$_3$)$_3$ | |
| 122 | (CH$_2$)$_3$ | 4-Chlorocyclohexyl | H | H | |
| 123 | (CH$_2$)$_3$ | 4-Chlorocyclohexyl | H | —CH$_2$(p-C$_6$H$_4$)C(CH$_3$)$_3$ | |
| 124 | (CH$_2$)$_3$ | 4-Aminocyclohexyl | H | H | |
| 125 | (CH$_2$)$_3$ | 2-Piperidyl | H | H | |
| 126 | (CH$_2$)$_3$ | 2-(1-Methylpiperidyl) | H | H | |
| 127 | (CH$_2$)$_3$ | 4-Piperidyl | H | H | |
| 128 | (CH$_2$)$_3$ | 4-(1-Methylpiperidyl) | H | H | |
| 129 | (CH$_2$)$_4$ | Cyclohexyl | H | H | |
| 130 | (CH$_2$)$_4$ | Cyclohexyl | H | —CH$_2$(p-C$_6$H$_4$)C(CH$_3$)$_3$ | |
| 131 | (CH$_2$)$_4$ | 4-Methylcyclohexyl | H | H | 162° C./0.3 mm |
| 132 | (CH$_2$)$_4$ | 4-Methylcyclohexyl | H | —CH$_2$(p-C$_6$H$_4$)C(CH$_3$)$_3$ | |
| 133 | (CH$_2$)$_4$ | 4-Methylcyclohexyl | —CH$_2$CH(CH$_3$)OCH(CH$_3$)CH$_2$— | | 198–210° C./0.4 mm |
| 134 | (CH$_2$)$_4$ | 4-tert.-Butylcyclohexyl | H | H | |
| 135 | (CH$_2$)$_4$ | 4-tert.-Butylcyclohexyl | H | —CH$_2$(p-C$_6$H$_4$)C(CH$_3$)$_3$ | |
| 136 | (CH$_2$)$_2$CH(C$_6$H$_{11}$)CH$_2$ | Cyclohexyl | H | H | |
| 137 | —NH(CH$_2$)$_3$— | Cyclohexyl | H | H | |
| 138 | —N(CH$_3$)(CH$_2$)$_3$— | Cyclohexyl | H | H | |
| 139 | —N(CH$_3$)(CH$_2$)$_3$— | Cyclohexyl | H | —CH$_2$(p-C$_6$H$_4$)C(CH$_3$)$_3$ | |
| 140 | —N(CH$_3$)(CH$_2$)$_3$— | Cyclohexyl | H | —CH$_2$(CH$_2$)$_2$CH$_2$— | |
| 141 | —(CH$_2$)$_3$C(CH$_3$)$_2$— | H | H | H | 154–156° C./1 mm |
| 142 | —[C(CH$_3$)$_2$]$_2$— | H | H | H | |
| 143 | (CH$_2$)$_7$ | H | H | H | 110–114° C./0.7 mm |
| 144 | (CH$_2$)$_7$ | H | H | —CH$_2$(p-C$_6$H$_4$)C(CH$_3$)$_3$ | |
| 145 | (CH$_2$)$_7$ | H | —CH$_2$(CH$_2$)$_2$CH$_2$— | | 0.8 mm |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton,
Ustilago species in cereals and sugar cane,
*Venturia inaequalis* (scab) in apples,
*Septoria nodorum* in wheat,
*Botrytis cinerea* (gray mold) in strawberries and grapes,
*Cercospora arachidicola* in groundnuts,
*Pseudocerosporella herpotrichoides* in wheat and barley,
*Pyricularia oryzae* in rice,
*Phytophthora infestans* in potatoes and tomatoes,
*Plasmopara viticola* in grapes, and
Fusarium and Verticillium species in various plants.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as a solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (eg., ethanolamine, dimethyformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt% of active ingredient.

The application rates are from 0.02 to 3 kg or more of active ingredient per hectare, depending on the type of effect desired. The novel compounds may also be used for protecting materials for instance against *Paecilomyces variotti*, and for combating wood-destroying fungi such as *Coniophora puteana* and *Polystictus versicolor*. The novel active ingredients may also be used as fungicidal components of oily wood preservatives for protecting wood against wood-discoloring fungi. They are applied by treating, for example impregnating or painting, the wood with them.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 2 is mixed with 10 parts by weight of N-methyl-α-pyrrolidone. A mixture is obtained which is suitable for application in the form of very fine drops.

II. 20 parts by weight of compound no. 23 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 63 is dissolved in a mixture consisting of 40 parts by weight of cyclohexane, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 71 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 75 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly the mixture in water, a spray liquor is obtained.

VI. 3 parts by weight of compound no. 78 is intimately mixed with 97 parts by weight of particulate kaolin. A dust is obtained containing 3% by weight of the active ingredient.

VII. 30 parts by weight of compound no. 102 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 142 is intimately mixed with 10 parts of the sodium salt of a phenolsulfonic acid-urea-formaldehyde condensate, 2 parts of silica gel and 48 parts of water to give a stable aqueous dispersion. Dilution in water and gives an aqueous dispersion.

IX. 20 parts by weight of compound no. 148 is intimately mixed with 2 parts by weight of the calcium salt of dodecylbenzenesulfonic acid, 8 parts by weight of a fatty alcohol polyglycol ether, 2 parts by weight of the sodium salt of a phenosulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
  dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithioccarbamate and
N,N'-polypropylenebis(thiocarbamyl) disulfide;
  nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
  heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene, 4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclodecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-diemthylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

Use Examples

The prior art compounds used for comparison purposes were N-benzyl-trans-4-tert-butylcyclohexylamine (A) disclosed in J. Org. Chem., 48, 3412, 1983, and N-tridecyl-2,6-dimethylmorpholine (B) disclosed in DE 11 64 152 and DC 11 73 722.

Use Example 1

Action on wheat mildew

Leaves of pot-grown wheat seedlings of the "Frü gold" variety were sprayed with aqueous liquors containing (dry basis) 80% of active ingredient and 20% of emulsifier, and sprayed, 24 hours after the sprayed-on layer had dried, with spores of wheat mildew (*Erysiphe graminis* var. *tritici*). The plants were then set up in the greenhouse at 20° to 22° C. and a relative humidity of 75 to 80%. The extent of mildew spread was assessed after 7 days.

In this experiment, formulations containing 0.025 and 0.006% of active ingredients 2, 73, 63, 71, 75, 78, 44 and 102 substantially prevented injurious fungi from developing, whereas comparative agents A and B did not prevent heavy attack (untreated=total attack).

Use Example 2

Action on cucumber mildew (curative)

Leaves of pot-grown cucumber seedlings of the "Chinesische Schlange" variety were sprayed at the two-leaf stage with an aqueous conidial suspension of cucumber mildew. One day later, these plants were sprayed to runoff with aqueous liquors containing (dry basis) 80% of active ingredient and 20% of emulsifier. The plants were then set up in the greenhouse at 20° to 22° C. and a relative humidity of 70 to 80%. The extent of fungus spread was determined 21 days after inoculation.

In this experiment, leaf attack after treatment with a 0.025% formulation of compounds 2, 23, 26, 63, 71, 75, 78, 54, 101 and 102 was slight, whereas comparative agents A and B were unable to prevent heavy attack (untreated=total attack).

Use Example 3

Action on *Botrytis cinerea* in pimientos

Pimiento seedlings of the "Neusiedler Ideal Elite" variety were sprayed, after 4 and 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a gread extent on the untreated plants that the necroses covered the major portion of the leaves.

In this experiment, leaf attack was low after treatment with a 0.05% formulation of active ingredients 14, 18, 22, 25, 26, 53, 66, 72, 82, 98, 100, 104, 105, 110, 131 and 141, whereas total attack occurred after treatment with comparative agents A and B.

Use Example 4

Action on *Septoria nodorum*

Leaves of pot-grown wheat seedlings of the "Jubilar" variety were sprayed to runoff with aqueous liquors containing (dry basis) 80% of active ingredient and 20% of emulsifier. On the following day the plants were infected with an aqueous spore suspension of *Septoria nodorum* and further cultivated for 7 days at 17° to 19°

C. and a relative humidity of 95%. The extent of fungus spread was then assessed visually.

In this experiment, leaf attack after treatment with a 0.05% formulation of active ingredients 14, 18, 22, 25, 26, 53, 59, 66, 72, 73, 82, 98, 100, 101, 105, 110, 131, 141 and 143 was slight, whereas heavy attack occurred after treatment with comparative agents A and B.

We claim:

1. A cyclohexylamine compound of the formula:

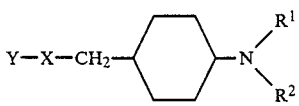

wherein:
X is a single bond or an alkylene chain of 1 to 12 carbon atoms which is unsubstituted or substituted by one or more alkyl groups, each of 1 to 5 carbon atoms, and in which said alkylene chain, 1 to 4 carbon atoms may be replaced by O, S or N;

Y is hydrogen, aryl, cyclohexyl, 4-cyclohexylcyclohexyl, or perhydro-1- or -2-naphthyl which may be substituted by one, two or three alkyl, alkoxy, alkylthio or alkylamino groups of 1 to 12 carbon atoms or by one, two or three halogen, amino, hydroxy or trifluoromethyl groups, and $R^1$ and $R^2$ are identical or different and independently of one another are each hydrogen, alkyl, alkenyl, alkynyl, hydroxyalkyl, cycloalkyl, cycloalkenyl or aralkyl of 1 to 12 carbon atoms, which in turn may be substituted by one, two or three alkyl, alkenyl, alkynyl, alkoxy or alkylthio radicals of 1 to 4 carbon atoms or cyclohexyl or 4-tert-butylcyclohexyl; and addition salts of said cyclohexyl amine compounds with acids;

wherein when $R^1$, $R^2$, and Y are all hydrogen, X is a single bond or an alkylene chain of 1–3, 5 or 8–12 carbon atoms which is unsubstituted or an alkylene chain of 1 or 3–12 carbon atoms which is substituted by one or more alkyl groups, each of 1 to 5 carbon atoms, or X is an alkylene chain of 1 to 12 carbon atoms which is unsubstituted or substituted by one or more alkyl groups, each of 1 to 5 carbon atoms, and in which alkylene chain, 1 to 4 carbon atoms are replaced by O, S or N;

with the exception of those compounds in which X is a single bond, Y is cyclohexyl and $R^1$ and $R^2$ are each hydrogen or $R^1$ and $R^2$ are each methyl.

2. The compound of claim 1, where X is a methylene or a 1,2-ethylene group, Y is cyclohexyl and $R^1$ and $R^2$ are hydrogen.

3. The compound of claim 1, where X is a methylene or a 1,2-ethylene group, Y is perhydronaphthyl and $R^1$ and $R^2$ are hydrogen.

4. The compound of claim 1, wherein X is one member selected from the group consisting of methylene, ethylene, 1,2-propylene, 1,3-propylene, 1,3-butylene, 1,4-butylene, 2-alkyl-1,3propylene, 2,2-dialkyl-1,3-propylene, 1,5-pentylene, 2-alkyl-1,4-butylene, 2-alkyl-1,5-pentylene, 3-alkyl-1,5-pentylene, 1,6-hexylene, 2-alkyl-1,6-hexylene, 1,7-heptylene, 1,8-octylene, 1,9-nonylene, 1,10-decylene, 1,11-undecylene, 1,12-dodecylene, methyleneoxy, ethyleneoxy, propyleneoxy, butyleneoxy, pentyleneoxy, hexyleneoxy, heptyleneoxy, octyleneoxy, nonyleneoxy, decyleneoxy, undecyleneoxy, dodecyleneoxy, ethyleneamino, propyleneamino, and N-$C_1$-$C_4$-alkylpropyleneamino.

5. The compound of claim 1, wherein Y is one member selected from the group consising of hydrogen, phenyl, $C_1$-$C_4$-alkylphenyl, cyclohexyl, $C_1$-$C_4$-alkylcyclohexyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-n-butylcyclohexyl, 2-, 3- and 4-tert-butylcyclohexyl, 4-cyclohexylcyclohexyl, dimethylcyclohexyl, methylethylcyclohexyl, methylisopropylcyclohexyl, methyl-tert-butylcyclohexyl, diethylcyclohexyl, ethylisopropylcyclohexyl, ethyl-tert-butylcyclohexyl, halocyclohexyl, 2-, 3- and 4-chlorocyclohexyl, 2-, 3- and 4-fluorocyclohexyl, 2-, 3- and 4-trifluoromethylcyclohexyl, 2-, 3- and 4-aminocyclohexyl, $C_1$-$C_{12}$-alkylaminocyclohexyl, $C_2{14}$ $C_{24}$-dialkylaminocyclohexyl, hydroxycyclohexyl, $C_1$-$C_{12}$-alkoxycyclohexyl, $C_1$-$C_{12}$-alkylthiocyclohexyl, perhydro-1-naphthyl, and perhydro-2-naphthyl.

6. The compound of claim 1, wherein $R^1$ and $R^2$ is each independently one member selected from the group consisting of methyl, ethyl, straight-chain or branched propyl, butyl, pentyl, hexyl, heptyl, octyl, nonyl, decyl, 2-hydroxypropyl, $C_2$-$C_5$-alkenyl, allyl, methallyl, pentenyl, cyclopentyl, cyclohexyl, cyclohexylmethyl, tert-butylcyclohexylmethyl, methcyclohexyl, tert-butylcyclohexyl, cycloheptyl, cyclooctyl, benzyl, $C_1$-$C_4$-alkylbenzyl, methylbenzyl, ethylbenzyl, dimethylbenzyl, methylethylbenzyl, isopropylbenzyl and tert-butylbenzyl.

7. A fungicide containing a solid or liquid carrier and a cyclohexylamine compound of the formula:

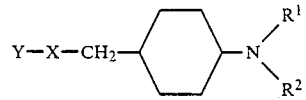

wherein:
X is a single bond or an alkylene chain of 1 to 12 carbon atoms which is unsubstituted or substituted by one or more alkyl groups, each of 1 to 5 carbon atoms, and in which said alkylene chain, 1 to 4 carbon atoms may be replaced by O, S or N;

Y is hydrogen, aryl, cyclohexyl, 4-cyclohexylcyclohexyl, or perhydro-1- or -2-naphthyl which may be substituted by one, two or three alkyl, alkoxy, alkylthio or alkylamino groups of 1 to 12 carbon atoms or by one, two or three halogen, amino, hydroxy, or trifluoromethyl groups;

$R^1$ and $R^2$ are identical or different and independently of one another are each hydrogen, alkyl, alkenyl, alkynyl, hydroxyalkyl, cycloalkyl, cycloalkenyl or aralkyl of 1 to 12 carbon atoms, which in turn may be substituted by one, two or three alkyl, alkenyl, alkynyl, alkoxy or alkylthio radicals of 1 to 4 carbon atoms or cyclohexyl or 4-tert-butylcyclohexyl; and addition salts of said cyclohexylamine compound with acids;

with the exception of those compounds in which X is a single bond, Y is cyclohexyl and $R^1$ and $R^2$ are each hydrogen or $R^1$ and $R^2$ are each methyl.

8. The fungicide of claim 7, where X is a methylene or a 1,2-ethylene group, Y is cyclohexyl and $R^1$ and $R^2$ are hydrogen.

9. The fungicide of claim 7, where X is a methylene or a 1,2-ethylene group, Y is perhydronaphthyl and $R^1$ and $R^2$ are hydrogen.

10. The fungicide of claim 7, where X is one member selected from the group consisting of methylene, ethylene, 1,2-propylene, 1,3-propylene, 1,3-butylene, 1,4-butylene, 2-alkyl-1,3-propylene, 2,2-dialkyl-1,3-propylene, 1,5-pentylene, 2-alkyl-1,4-butylene, 2-alkyl-1,5-pentylene, 3-alkyl-1,5-pentylene, 1,6-hexylene, 2-alkyl-1,6-hexylene, 1,7-heptylene, 1,8-ocytlene, 1,9-nonylene, 1,10-decylene, 1,11-undecylene, 1,12-dodecylene, methyleneoxy, ethyleneoxy, propyleneoxy, butyleneoxy, pentyleneoxy, hexyleneoxy, heptyleneoxy, octyleneoxy, nonyleneoxy, decyleneoxy, undecyleneoxy, dodecyleneoxy, ethyleneamino, propyleneamino, and N-$C_1$-$C_4$-alkylpropyleneamino.

11. The fungicide of claim 7, wherein Y is one member selected from the group consisting of hydrogen, phenyl, $C_1$-$C_4$-alkenylphenyl, cyclohexyl, $C_1$-$C_4$-alkylcyclohexyl, 2-, 3- and 4-methylcyclohexyl, 2-, 3- and 4-ethylcyclohexyl, 2-, 3- and 4-propylcyclohexyl, 2-, 3- and 4-isopropylcycohexyl, 2-, 3- and 4-n-butylcyclohexyl, 2-, 3- and 4-tert-butylcyclohexyl, 4-cyclohexylcyclohexyl, dimethylcyclohexyl, methylethylcyclohexyl, methylisopropylcyclohexyl, methyl-tert-butylcyclohexyl, diethylcyclohexyl, ethylisopropylcyclohexyl, ethyl-tert-butylcyclohexyl, halocyclohexyl, 2-, 3- and 4-chlorocyclohexyl, 2-, 3- and 4-fluorocyclohexyl, 2-, 3- and 4-trifluoromethylcyclohexyl, 2-, 3- and 4-aminocyclohexyl, $C_1$-$C_{12}$-alkylaminocyclohexyl, $C_2$-$C_{24}$-dialkylaminocyclohexyl, hydroxycyclohexyl, $C_1$-$C_{12}$-alkoxycyclohexyl, $C_1$-$C_{12}$-alkylthiocyclohexyl, perhydro-1-naphthyl, and perhydro-2-naphthyl.

12. The fungicide of claim 7, wherein $R^1$ and $R^2$ is each independently one member selected from the group consisting of methyl, ethyl, straight-chain or branched propyl, butyl, pentyl, hexyl, heptyl, octyl, nonyl, decyl, 2-hydroxypropyl, $C_2$-$C_5$-alkenyl, allyl, methallyl, pentenyl, cyclopentyl, cyclohexyl, cyclohexylmethyl, tert-butylcyclohexylmethyl, methcyclohexyl, tert-butylcyclohexyl, cycloheptyl, cyclooctyl, benzyl, $C_1$-$C_4$-alkylbenzyl, methylbenzyl, ethylbenzyl, dimethylbenzyl, methylethylbenzyl, isopropylbenzyl and tert-butylbenzyl.

* * * * *